(12) United States Patent
Davis et al.

(10) Patent No.: US 12,054,685 B1
(45) Date of Patent: Aug. 6, 2024

(54) COUPLING HIGH YIELD BIOCHEMICAL INTERMEDIATES FOR FUEL PRODUCTION

(71) Applicant: National Technology & Engineering Solutions of Sandia, LLC, Albuquerque, NM (US)

(72) Inventors: Ryan Wesley Davis, San Jose, CA (US); Eric Monroe, Waltham, MA (US); Joseph Carlson, Castro Valley, CA (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 478 days.

(21) Appl. No.: 16/929,439

(22) Filed: Jul. 15, 2020

(51) Int. Cl.
| | |
|---|---|
| *C10L 1/02* | (2006.01) |
| *C07C 67/08* | (2006.01) |
| *C07C 67/317* | (2006.01) |
| *C10L 1/19* | (2006.01) |

(52) U.S. Cl.
CPC .............. *C10L 1/02* (2013.01); *C07C 67/08* (2013.01); *C07C 67/317* (2013.01); *C10L 1/19* (2013.01); *C10L 2200/0484* (2013.01); *C10L 2290/24* (2013.01)

(58) Field of Classification Search
CPC ...... C10L 1/02; C10L 1/19; C10L 2200/0484; C10L 2290/24; C07C 67/08; C07C 67/317
See application file for complete search history.

(56) References Cited

U.S. PATENT DOCUMENTS

| | | | |
|---|---|---|---|
| 5,281,691 A | 1/1994 | Hubbs et al. | |
| 5,612,303 A * | 3/1997 | Takayanagi | C09D 7/20 |
| | | | 134/40 |

(Continued)

OTHER PUBLICATIONS

Moat, et al., "Fermentation Pathways", In Microbial Physiology, 2002, pp. 412-433.

(Continued)

*Primary Examiner* — Ellen M McAvoy
*Assistant Examiner* — Ming Cheung Po
(74) *Attorney, Agent, or Firm* — Madelynne Farber; Eschweiler & Potashnik, LLC; Samantha Updegraff

(57) ABSTRACT

A chemical upgrading of two high-yield fermentation products to produce a novel biofuel with properties desirable for use in internal combustion engines produces a $C_7$ to $C_{22}$ alkoxyalkanoate corresponding to formula (I):

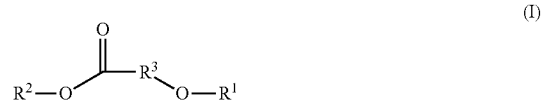

wherein $R^2$ and $R^1$ are alkyl groups independently selected to have 2 to 18 carbon atoms;
wherein the $R^3$ group is a $C_1$ to $C_5$ group divalent alkyl group. The alkoxyalkanoate can be used as a neat fuel or blend with biodiesel, diesel, gasoline, ethanol or other fuels. The alkoxyalkanoates have improved cloud point properties over diesel fuels. A method for making the alkoxyalkanoate from a biomass source is also disclosed.

20 Claims, 6 Drawing Sheets

(56) References Cited

U.S. PATENT DOCUMENTS

| | | | | |
|---|---|---|---|---|
| 8,377,151 B2* | 2/2013 | McMurry | ................ | C10L 1/02 |
| | | | | 44/307 |
| 2010/0076223 A1* | 3/2010 | Shiraki | ................ | C07C 231/02 |
| | | | | 564/136 |
| 2011/0107660 A1* | 5/2011 | Chen | ........................ | C10L 1/19 |
| | | | | 44/400 |

OTHER PUBLICATIONS

Wang, et al., "Autoignition of Trans-Decalin, a Diesel Surrogate Compound: Rapid Compression Machine Experiments and Chemical Kinetic Modeling", Combustion and Flame, vol. 194, Nov. 28, 2017, 34 pages.

* cited by examiner

| Compound Name | Chemical Structure | Derived Cetane Number | Lower Heating Value (MJ/kg) | Yield Sooting Index (YSI) | Cloud Point (°C) |
|---|---|---|---|---|---|
| Soy Biodiesel* | 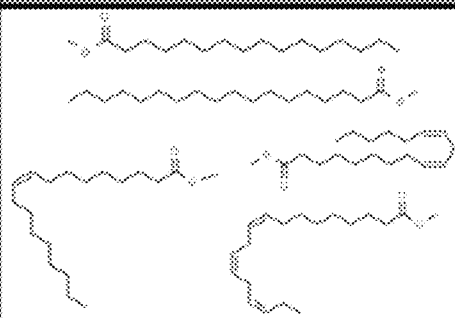 | 52 | 37 | 126 | 0.5 |
| Isopentyl 2-(isopentyloxy) propanoate | 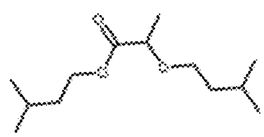 | 43.6 | 34.5 | 86 | <-50 |

COUPLING HIGH YIELD BIOCHEMICAL INTERMEDIATES FOR FUEL PRODUCTION

STATEMENT OF GOVERNMENTAL INTEREST

This invention was made with Government support under Contract No. DE-NA0003525 awarded by the United States Department of Energy/National Nuclear Security Administration. The Government has certain rights in the invention.

FIELD

This disclosure relates to biomass constituent conversion into fuel and fuel blending agents. More specifically, this disclosure relates to fuel and fuel blending agents for internal combustion engines.

BACKGROUND

Combustion of liquid fossil fuels for transportation is a major source of carbon emissions. Biofuels are increasingly used to supplement conventional petroleum-derived fuels for transportation. As a renewable energy source, biofuels help to reduce dependence on fossil-fuel, mitigate greenhouse-gases emissions, and in some cases, improve air quality. New renewable transportation fuels derived from abundant sources of biomass will be needed to further offset fossil fuel use. Mandates for biofuels have been established around the world, requiring an even larger increase in biofuel usage in the future. For example, to support the growing desire to reduce greenhouse gas emissions and establish energy independence, the United States is mandated by federal law to produce 1 billion gallons a year of renewable transportation fuel.

Biodiesel is defined as "a fuel comprised of monoalkyl esters of long-chain fatty acids derived from vegetable oils or animal fats, designated B100." Standard Specification for Biodiesel Fuel Blend Stock (B100) for Middle Distillate Fuels. In ASTM D6751-19, 2019. Biodiesel is typically produced using methanol by conversion of triglycerides into fatty acid methyl esters (FAMEs), where the fatty acid profile of the lipid source used will determine the fuel properties. While biodiesel has successfully penetrated the fuel market, with production reaching 2.2 billion gallons in 2016, poor performance in important fuel properties such as cold flow continues to limit the application of large blend volumes in cold weather environments. See Shrestha, D.; Van Gerpen, J.; Thompson, J.; Zawadzki, A. in Cold flow properties of biodiesel and effect of commercial additives, 2005 ASAE Annual Meeting, 2005; American Society of Agricultural and Biological Engineers: 2005; p 1; Monirul, I.; Masjuki, H.; Kalam, M.; Zulkifli, N.; Rashedul, H.; Rashed, M.; Imdadul, H.; Mosarof, M., A comprehensive review on biodiesel cold flow properties and oxidation stability along with their improvement processes, RSC advances 2015, 5, (105), 86631-86655; and Bolonio, D.; Llamas, A.; Rodríguez-Fernández, J.; Al-Lal, A. M.; Canoira, L.; Lapuerta, M.; Gómez, L., Estimation of cold flow performance and oxidation stability of fatty acid ethyl esters from lipids obtained from *Escherichia coli*. Energy & Fuels 2015, 29, (4), 2493-2502. Cold temperatures cause typical biodiesel fuels to gel and clog fuel filters. Today's highest-volume commercial MCCI (mixing-controlled compression ignition) biofuel, lipid-based biodiesel, typically exhibits poor cold-weather performance that limits its use in much of the world. Yet bioderived intermediates and fermentation products are typically unsuitable for use in MCCI engines or cannot be produced at high rates, yields, and titers. To address these challenges, efforts have been made to discover new bioderived fuels for diesel engines that have improved fuel properties.

SUMMARY

Disclosed herein is a chemical upgrading of two high-yield fermentation products to produce a novel biofuel with properties desirable for use in mixing-controlled compression ignition (MCCI) engines. In particular, upgrading of hydroxyalkanoate (e.g., glycolic acid, lactic acid, and 4-hydroxybutyrate) with varying (fusel) alcohols was accomplished to provide a class of compounds that show promise as a diesel alternative in autoignition (compression ignition) engines and also found to have favorable properties for spark ignition engines. For autoignition engines, these properties include low cloud point, low sooting index, high energy content, and high cetane (DCN).

In addition to the promising fuel properties, the theoretical production yield for these molecules have the potential to exceed that of ethanol from neat sugars and can incorporate low-quality biomass hydrolysates. Hydroxyalkanoates are readily available by microbial fermentation; therefore, fuels derived from hydroxyalkanoate feedstocks may permit broader use of renewable diesel fuels.

In an embodiment, a fuel for an internal combustion engine comprises a $C_7$ to $C_{22}$ alkoxyalkanoate corresponding to formula (I):

The $R_2$ and $R_1$ are alkyl groups independently selected to have 2 to 18 carbon atoms; and the $R_3$ group is a $C_1$ to $C_5$ divalent alkyl group.

The compounds described herein may be used as neat fuels or mixed fuels (with diesel, biodiesel, marine fuel or other fuel compounds) in autoignition or spark ignition engines, such as diesel engines, gasoline (spark ignition) engines, MCCI, Homogeneous Charge Compression Ignition (HCCI) engines, or more generally in Low-Temperature Gasoline Combustion (LTGC) engines (using gasoline-like fuels), that have the high-efficiency advantages of HCCI but can operate with some level of charge inhomogeneities.

In an embodiment, a blended fuel for an internal combustion engine comprises the compound from formula I above and a fuel selected from the group consisting of: gasoline, diesel, alcohol fuel, biofuel, Fischer-Tropsch fuel, or combinations thereof.

In an embodiment, an enhanced fuel for an internal combustion engine includes the alkoxyalkanoate and a portion of a fuel selected from the group consisting of: diesel, gasoline, alcohol fuel, biofuel, marine fuel, Fischer-Tropsch fuel, or combinations thereof; and a portion of an alkoxyalkanoate compound.

In an embodiment, a method for powering an internal combustion engine includes the steps of combusting a fuel to drive a piston in a cylinder of the engine. In an embodiment, a method for making a fuel product for an internal combustion engine at least partially from a biomass source, the method comprising: reacting a fusel alcohol and hydroxyalkanoate in a solvent to form a hydroxyalkanoate;

and reacting the hydroxyalkanoate with an alkyl halide to form an alkoxyalkanoate. The alkoxyalkanoate is a $C_7$ to $C_{22}$ alkoxyalkanoate.

The term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form. Additionally, as used herein, the term "exemplary" is intended to mean serving as an illustration or example of something and is not intended to indicate a preference.

In an embodiment, a fuel composition consists essentially of the alkoxyalkanoate reaction product. "Consisting essentially of" in this instance, means the specified materials and those that do not materially affect the basic and novel characteristics of the methods, articles of manufacture, or compositions listed herein. For example, an unspecified material that does not materially affect the basic and novel characteristics of the methods, articles of manufacture, or compositions listed herein, in an amount of less than about 5%, less than about 3%, or less than about 1% may be encompassed by this term.

DETAILED DESCRIPTION

Figure 1:
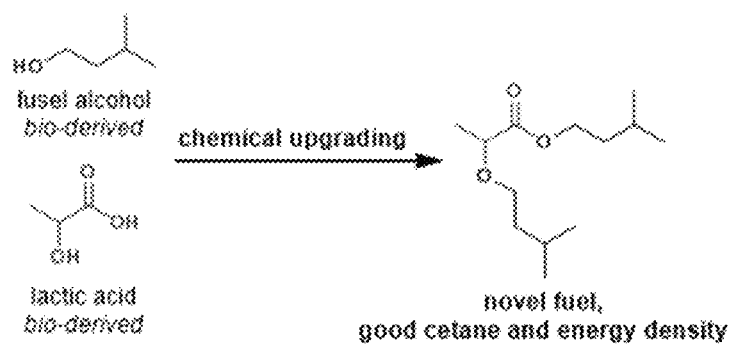
FIG. 1 is a graphic showing an example coupling reaction to form an alkoxyalkanoate and a comparison table of properties.

Demonstrated herein is a new approach to address biofuel insufficiencies, such as those mentioned above, by combining compounds readily available from biomass sources, that is: hydroxyalkanoates and fusel alcohols. Fermentation can convert sugars into lactic acid at a 97% mass yield, and various biomass intermediates can be converted into fusel alcohols at mass yields up to 60%, such as 40 to 55%, or 45 to 50%. Both products can also be produced rapidly, cheaply, and at high concentrations from a wide range of biomass feedstocks using established industrial processes. However, neither product alone has properties suitable for MCCI fuel.

Thus, the two products were combined and upgraded via esterification followed by etherification, resulting in a $C_7$-$C_{22}$ alkoxyalkanoate, such as the compound isopentyl 2-(isopentyloxy)propanoate. Testing of this and other compounds revealed desirable properties for MCCI. A cloud point (the temperature at which liquid begins to solidify) of less than −50° C. also suits it for cold-weather operation—a major advantage over traditional biodiesel. It is believed that these improvements are due to increased chemical branching and increased oxygen content.

The combined biological and chemical synthesis pathway converts cellulosic biomass at overall mass yields up to 68% (based on the linear additive theoretical pathway yields of each intermediate). For comparison, the overall mass yield of cellulosic ethanol's production pathway is only 45%. Accordingly, the presently described process and product provides for a substantial improvement in the use of renewable biomass products for fuels.

An advantage of biofuels are the renewable resources, such as biomass, available as starting materials. Sources of biomass include dedicated energy crops, such as herbaceous or woody crops; crop residues, such as stalks and leaves of agricultural crops; forestry residues, such as unmerchantable timber remnants; and even algal or cyanobacterial feedstocks. Other sources include wood processing residues, such as sawdust; municipal waste, such as sorted recyclable materials; or wet waste, such as food waste and sewage. The biomass source should be amenable to solubilization and hydrolysis of biopolymers contained therein.

In general, the biomass should be pretreated to solubilize and hydrolyze the biopolymers (e.g., cellulose or proteins). This can be done by dilute acid hydrolysis. The hydrolysate should be pH adjusted from about 0 to about 5.2 for fermentation, such as 2 to 5, or 3 to 4.5.

Conversion of raw biomass to the starting material of the novel process disclosed can be accomplished by conversion of hydrolysates in the biomass using biological catalysts (including, e.g., *Saccharomyces, E. coli, Lactobacillus, Clostridium*, and a host of others). This generates a variety of common high-yielding intermediates from various acidogenic and solvetogenic biochemical pathways in homo- or heterofermentative processes. See Chapter 11: Fermentation Pathways, Microbial Physiology. Albert G. Moat, John W. Foster and Michael P. Spector (2002). ISBN: 0-471-39483-1, incorporated herein by reference. Furthermore, recent advances in synthetic biology and metabolic engineering significantly expand the ability to generate a host of biochemical intermediates with substantially improved bioconversion rates, yields, and titers. See Choi, et al, "Systems Metabolic Engineering Strategies: Integrating Systems and Synthetic Biology with Metabolic Engineering," Trends in Biol. Vol. 37, 8, p. 817-837, Aug. 1, 2019, incorporated herein by reference.

Among the biochemical compounds within 1-2 enzymatic steps from central metabolism are a variety of short-chain ($C_2$-$C_5$) hydroxyalkanoates, such as: alpha-hydroxy-acids, including lactate, glycolate, alpha-hydroxy butyrate, and alpha-hydroxy valerate; gamma-hydroxy acids, including 3-hydroxy-propionate, and 4-hydroxy-butyratre; and various short-chain ($C_2$-$C_5$) alcohols, including ethanol, (iso) propanol, (iso)butanol, and (iso)pentanols, commonly denoted as 'fusel' alcohols. See Noor, et al, "Central Carbon Metabolism as a Minimal Biochemical Walk between Precursors for Biomass and Energy," Molecular Cell Vol. 39 Iss. 5, p. 809-820 (Sep. 10, 2010), incorporated herein by reference.

To valorize the biomass intermediates, chemical coupling of the various hydroxyalkanoic acids and fusel alcohols retrieved from biomass was performed. The coupling was performed at the alcohol and acid reactive sites to generate a suite of hetero-bifunctional conjugates exhibiting ether and ester moieties, with stoichiometries of 1 hydroxyalkanoate: 2 alcohols. Alkyl halides were generated from the fusel alcohols to make the final alkoxyalkanoate products. An example overall reaction scheme is shown in FIG. 1. FIG. 1 shows the fusel alcohol component, in this case, (iso) butanol, and the hydroxyalkanoate component, in this case, lactic acid. These can be coupled and upgraded to an alkoxyalkanoate fuel compound in a two-step reaction.

In a first step shown in reaction scheme (1), the fusel alcohol and hydroxyalkanoate are combined with an acid catalyst, such as sulfuric acid, in a non-polar organic solvent, such as toluene.

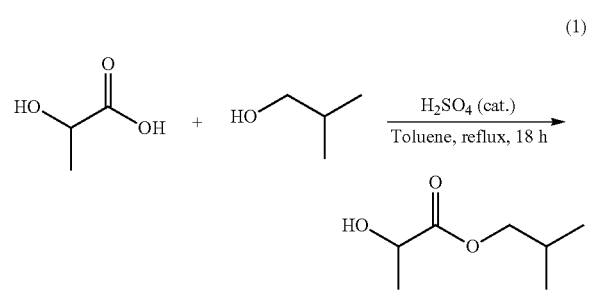

(1)

In an embodiment, the reactants are brought to reflux for several hours, such as 1 to 24 hours, e.g., 6 to 18 hours, or until substantial completion to produce an esterified intermediate product. The reaction can then be cooled, e.g., in an ice bath to lower than ambient temperature, (e.g. 0° C.) and quenched via slow addition of $H_2O$. The alkoxyalkanoate can be extracted using an organic non-polar solvent, such as hexanes, and washed with, e.g., $NaHCO_3$ and saturated salt (NaCl) solution. It can be dried (such as by using anhydrous $MgSO_4$), filtered, and concentrated in vacuo. The esterified product can be purified by methods such as flash chromatography and distillation.

In a second step shown in reaction scheme (2), the esterified intermediate product is further reacted with an alkyl halide (such as one derived from a fusel alcohol in the biomass) to produce the alkoxyalkanoate.

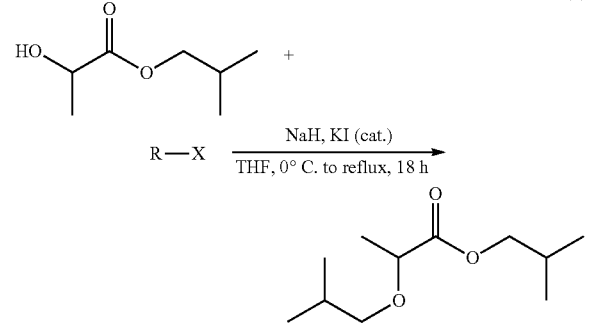

(2)

R—X in this case represents an alkyl halide. The alkyl group R of the alkyl halide corresponds to the $R^1$ group of formula (I) below. Here the $R^1$ group is an isobutyl group.

In an embodiment of this step, a NaH dispersion in mineral oil and THF can added to a reaction vessel and cooled to a temperature lower than ambient temperature (e.g., lower than 22° C.), such as about 0° C. The esterified product from reaction step 1 can then be added, such as in a metered manner over several minutes, e.g., 5 to 30 minutes, or 10 to 20 minutes, and stirred. Then, the desired alkyl halide and catalyst (here KI), can be added and the reaction mixture can be brought to reflux for several hours, such as 1 to 24 hours, e.g., 6 to 18 hours, or until substantial completion to produce the alkyl alkoxyalkanoate. The reaction can be cooled, e.g., in an ice bath to lower than ambient temperature, (e.g. 0° C.) and quenched via slow addition of water. The alkoxyalkanoate can be extracted using an organic non-polar solvent, such as hexanes, and washed with saturated salt (NaCl) solution. It can be dried (such as by using anhydrous $MgSO_4$), filtered, and concentrated in vacuo. The alkoxyalkanoate product may be purified further by chromatography on silica gel.

A similar procedure can be used for coupling other fusel alcohols and hydroxyalkanoate compounds.

Through the reactions, the OH groups on the lactic acid react to couple a fusel alcohol groups, displacing the OH group on the fusel alcohol. In the case of FIG. 1, isopentyl 2-(isopentyloxy)propanoate is formed with a good balance of properties with improvements over conventional soy biodiesel as shown in the Table accompanying the reaction scheme in FIG. 1. Soy biodiesel is a mixture of fatty acid methyl esters (FAME), which varies based on the soybean feedstock used. The five dominant FAME components in soy biodiesel are shown. Experimental values were measured based on a standard soy methyl ester sample described in the fuel property database at fuelsdb.nrel.gov.

The term alkoxyalkanoate is meant to encompass the reaction product of the process described herein where alkyl hydroxyalkanoate and a fusel alcohol are the starting materials, and a strong acid, such as, sulfuric acid or a catalytic quantity of alkyl halide reactant is also used. There are other chemistries for forming the product without the alkyl halide, but this is believed to be the most reliable approach that minimizes downstream separation. The alkoxyalkanoate is a $C_7$-$C_{22}$ alkoxyalkanoate with both ester and ether moieties, such as a $C_8$ to $C_{20}$ alkoxyalkanoate, or a $C_{10}$ to $C_{16}$ alkoxyalkanoate, as shown in Formula I.

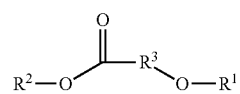

(I)

The $R^3$ group is a $C_1$ to $C_5$ divalent group, linear or branched. In most examples below, $R^3$ is a $C_2$ alkyl group with a branched methyl group, i.e.:—$CH(CH_3)$—. $R_3$ can also be, for example, —$CH_2CH_2CH_2$— or —$CH_2$—. $R^1$ and $R^2$ are alkyl groups independently selected to have 2 to 18 carbon atoms. In an embodiment, the alkoxyalkanoate has a symmetrical carbon distribution, i.e., the same number of carbon atoms, such as 2 to 10 carbon atoms, or 3 to 8 carbon atoms in both $R^1$ and $R^2$. In an embodiment, $R^1$ and $R^2$ are non-symmetric, for example, wherein one of $R^1$ and $R^2$ is a $C_1$ or $C_2$ alkyl group, and the other is a $C_4$ to $C_8$ group. Several experiments were run to determine characteristics of different $R^1$ and $R^2$ alkyl group chain lengths, symmetry, and branching of these groups. In an embodiment, either or both $R^1$ and $R^2$ have 1 to 6, such as 2 to 5, or 3 to 4 branching methyl or ethyl or propyl groups. In an embodiment, either or both $R^1$ and $R^2$ have 1 to 5 units of unsaturation, such as 2 to 3 units of unsaturation. In an embodiment, either or both $R^1$ and $R^2$ have a cyclic group with 3 to 6 members, such as 4 to 5 members.

In an embodiment, $R^1$ is provided by an alkyl halide reactant and $R^2$ is provided by a fusel alcohol.

Table 1 shows several compounds made and tested for various properties to determine the effect of structure of the properties of the compound. Compounds with comparable C:O ratios but contrasting degrees of branching provide insight into the effect of substituents on fuel properties. These tests and examples are described further in the Examples section herein.

TABLE 1

| Compound | Structure |
|---|---|
| EXAMPLE-1 | 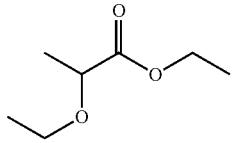 |
| EXAMPLE-2 | 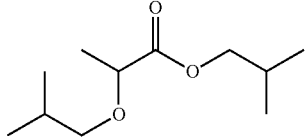 |
| EXAMPLE-3 | 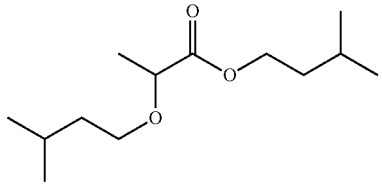 [SMILES: CC(C)CCOC(=O)C(C)OCCC(C)C] |
| EXAMPLE-4 | 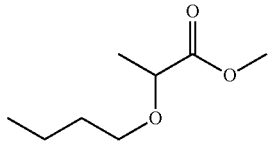 |
| EXAMPLE-5 | 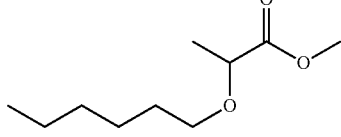 |
| EXAMPLE-6 | 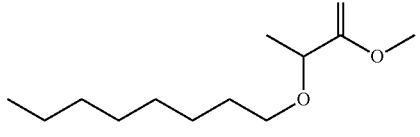 |
| EXAMPLE-7 | 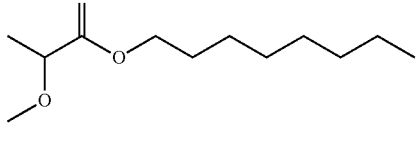 |
| EXAMPLE-8 | 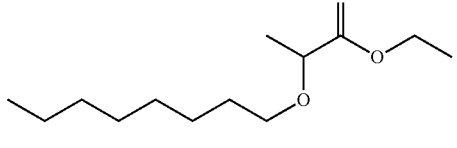 |
| EXAMPLE-9 | 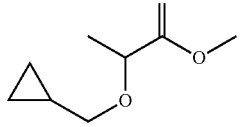 |

TABLE 1-continued

| Compound | Structure |
|---|---|
| EXAMPLE-10 | (structure) |
| EXAMPLE-11 | (structure) |
| EXAMPLE-12 | (structure) |

In Example 10, x is 1-8, and y is 0 to 3

The data herein indicates the alkoxyalkanoate compounds have some superior properties compared to biodiesel. For example, cloud point is a metric for evaluating the cold flow-properties of diesel fuels, these values go down to −10° C. to −60° C., such as −20° C. to −55° C., or −25° to −50° C. for the alkoxyalkanoates, which is a substantial improvement over conventional biodiesel. Furthermore, test results indicate that increasing degrees of branching on the $R^2$ and $R^1$ substituents will produce a 12% to 43% increase in cetane number. In addition, compared to conventional biodiesel, sooting is reduced by a factor of two without sacrificing cetane and energy density. This is in a bioderived performance additive that is only steps away from a renewable biomass feedstock.

Figure 7:
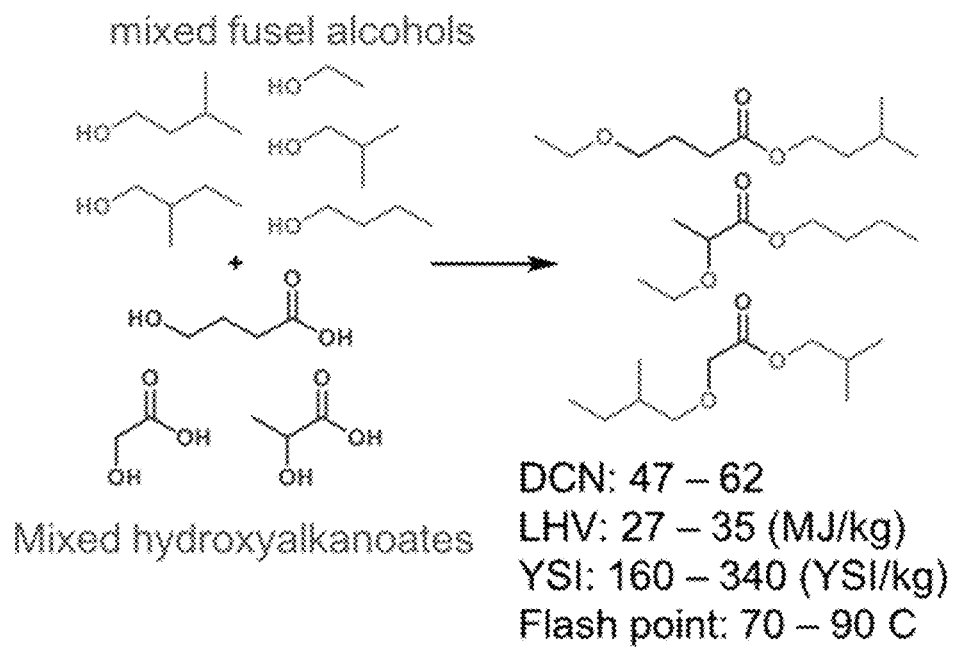
FIG. 7 is a graphic showing a scheme for formation of a mixture of compounds and example property ranges.

In an embodiment, a mixture of fusel alcohols and hydroxyalkanoates are combined to produce a mixture of fusel alkoxyalkanoates. An example, is shown in FIG. 7 with a range of properties that may result from such mixtures.

These results demonstrate the potential for the alkoxyalkanoate compounds to be used as neat fuels or in high blend volumes with diesel for use as all-weather fuels in autoignition engines, while also reducing soot emissions and increasing engine performance and fuel economy as compared to traditional biodiesel. The alkoxyalkanoates can also be used in gasoline blends or as neat or blended fuels for spark ignition engines.

In an embodiment, the alkoxyalkanoate compound has a derived cetane number (DCN) of 10 to 85, such as, for example, 20 to 65 to 110, or 45 to 60. This is compared to the DCN of B100 Biodiesel (comprising FAME compounds) of 62.6.

In an embodiment, the alkoxyalkanoate compound has a Cloud Point of −5° C. to −100° C., such as −10° C. to −60° C., or −25° to −50° C. This is contrasted to the cloud point of B100 Biodiesel of about −1° C.

In an embodiment, the alkoxyalkanoate compound has an LHV of 25 to 40 MJ/kg, such as, for example, 27 to 37 MJ/kg, or 30 to 35 MJ/kg. This compares to the LHV of B100 Biodiesel of 37.1 MJ/kg.

In an embodiment, the alkoxyalkanoate compound has a YSI (yield sooting index) of 10 to 160, such as, 20 to 90, or 40 to 80. This compares to the LHV of biodiesel of 500 to 1000 depending on the lipid feedstock. The YSI of a FAME soybean oil used as a standard commercial feedstock biodiesel is 550. (This is the same oil source as Example 10.)

In an embodiment, the alkoxyalkanoate compound has a C:O ratio (molar) of 2.33 to 7.34 C°, such as, for example, 2.66 to 6.67, or 3.66 to 4.67.

The examples disclosed herein indicate the compounds disclosed herein have improvements across multiple measured properties.

The examples herein are performed with neat examples of the alkoxyalkanoate compounds; however, the results indicate that the alkoxyalkanoate compounds can also be used as blending agents in traditional fuels in internal combustion engines.

In an embodiment, a fuel blend comprises a portion of an alkoxyalkanoate and a portion of a fuel selected from the group consisting of: gasoline, alcohols (for example, ethanol, methanol, or butanol), diesel fuel, biodiesel, marine fuel, or combinations thereof.

In an embodiment, the alkoxyalkanoate component comprises 51% to 99.9% of the total fuel by liquid volume, such as, for example, 60% to 98%, or 80% to 95%, and the minority portion of the fuel is a conventional fuel selected from those listed herein, for example, 5% to 0.01%, 20% to 5%, or 40% to 10% of the total fuel by liquid volume. In an embodiment, a majority portion alkoxyalkanoate is present with a minority conventional fuel in a volume ratio of 99.9:0.1 to 51:49, 95:5 to 70:30, or 90:10 to 60:40.

In another embodiment, the majority conventional portion fuel comprises 51% to 99.9% of the total fuel by liquid volume, such as, for example, 60% to 98%, or 80% to 95%, and the minority portion of the fuel is the alkoxyalkanoate, for example, 5% to 0.01%, 20% to 5%, or 40% to 10% of the total fuel by liquid volume. In an embodiment, the majority conventional portion fuel is present with the alkoxyalkanoate component in a volume ratio 99.9:0.1 to 51:49, 95:5 to 70:30, or 90:10 to 60:40.

In an embodiment, low-cost, conventional fuels may have certain fuel properties modified with the alkoxyalkanoate blending agent, so that the value is improved to a level that is advantageous in conventional commercial vehicles. In an embodiment, the alkoxyalkanoate compounds may also be used as a blending agent in fuels with lower DCN, such as currently available pump diesel fuels to create a fuel with a DCN above current levels for biodiesel. From the trends shown in the examples section, it is expected that the cloud point of the fuel blend can be lowered, for example, by 5 to 50° C., such as 10 to 20° C., or 15 to 30° C. lower than the cloud point of the conventional biodiesel fuel alone by adding an effective amount of the alkoxyalkanoate blending agent.

The blending of the gasoline, diesel, or alcohol fuel and the alkoxyalkanoate compound can be performed at the pump, for example, as a blending agent blended into the fuel in the underground containers at the filling station. In another example, two separate tanks at the filling station would be filled. One with majority portion fuel, e.g. gasoline or diesel, and one with the alkoxyalkanoate compound, and they would come together and be mixed in the pump, as the vehicle is fueled. The blending agent can also be added directly to the gas tank of a vehicle that is separately filled with fuel. It could also be blended at the supplier just prior to shipment to the filling station. In any of these manners the fuel blend could be changed depending on the climate/temperature of the season and filling location.

A method for powering an internal combustion engine includes combusting a fuel to drive a piston in a cylinder of the engine. The fuel comprises an alkoxyalkanoate compound selected from: diesel, gasoline, alcohol fuel, biofuel, marine fuel, Fischer-Tropsch fuel, or combinations thereof. In an embodiment, the alkoxyalkanoate compound is all or a majority portion of the total fuel used in the engine, particularly in autoignition engines.

In an embodiment, the alkoxyalkanoate compound is used in autoignition engines, such as diesel engines, MCCI, Homogeneous Charge Compression Ignition (HCCI) engines, or more generally in Low-Temperature Gasoline Combustion (LTGC) engines (using gasoline-like fuels), that have the high-efficiency advantages of HCCI but can operate with some level of charge inhomogeneities. The term LTGC includes HCCI and stratified, partially stratified, and spark-assisted variants that still provide the high efficiency and low emission of HCCI but work better over a wider operating range. See, for example, Dec, J. E., Yang, Y., Ji, C., and Dernotte, J., "Effects of Gasoline Reactivity and Ethanol Content on Boosted, Premixed and Partially Stratified Low-Temperature Gasoline Combustion (LTGC)," SAE technical paper no. 2015-01-0813, accepted for publication in the SAE J. of Engines, 2015 incorporated herein by reference. These engines are known in the art and do need description in detail to those of ordinary skill in the art.

A section including working examples follows, but, as with the rest of the detailed description, should not be read to be limiting on the scope of the claims.

EXAMPLES

Unless otherwise noted, all reactions were carried out in oven-dried glassware sealed with rubber septa under argon atmosphere with Teflon-coated magnetic stir bars. All reagents were purchased from Sigma Aldrich or Alfa Aesar and were used without further purification unless otherwise stated. Soy derived B100 was acquired from Louis Dreyfus (batch #20368) and used as received. All reactions were monitored by TLC, GCMS or NMR analysis. $^1$H spectra were referenced to residual solvent (Chloroform-d: 7.26 ppm, $^1$H). Chemical shifts are reported in parts per million, and multiplicities are indicated by s (singlet), d (doublet), t (triplet), q (quartet), quin (quintet), sex (sextet), m (multiplet), br (broad), and app (apparent). Coupling constants, J, are reported in Hertz. Visualization of analytical thin-layer chromatography was accomplished with UV (254) and potassium permanganate ($KMnO_4$) as a staining solution.

Comparative Example 1

Soy-derived B100 biodiesel fuel was acquired from Louis Dreyfus Agricultural Industries, LLC (batch #20368), and used as received with properties and composition detailed by Fioroni et al., Screening of potential biomass-derived streams as fuel blendstocks for mixing controlled compression ignition combustion. SAE International Journal of Advances and Current Practices in Mobility 2019, 1, (2019-01-0570), 1117-1138. This control example 1 material was used as a comparative example. The fatty acid profile for control Example 1 is shown in Table 1.

TABLE 2

| | Components of Comparative Example 1 | | | | | | | | |
|---|---|---|---|---|---|---|---|---|---|
| Fatty Acids | Myristic | Palmitic | Palmitoleic | Stearic | Oleic | Linoleic | Linolenic | Arachidic | Other |
| $C_{total}$:Unsaturation | 14:00 | 16:00 | 16:01 | 18:00 | 18:01 | 18:02 | 18:03 | 20:00 | |
| Composition$^a$ (% w/w) | 0.07 | 10.84 | 0.27 | 4.52 | 23.21 | 52.73 | 7.34 | 0.41 | 0.61 |

$^a$Normalized mass fractions are values based on GCMS analysis of the B100 blend.

Examples 1-12

Procedures for preparation of Examples 1-12 shown in Table 1 follows.

Lactate esters for Examples 2, 3, 7, 10, 11 and 12 were prepared by refluxing of the corresponding fusel alcohol with the corresponding hydroxy alkanoate (lactic acid, glycolic acid, or gamma-butyrolactone) in toluene with catalytic $H_2SO_4$, followed by distillation. DL-methyl lactate, L-ethyl lactate were used as received from Sigma Aldrich. Examples 1, 4-6, 8, and 9 were prepared in the same manner, however, the alcohols that were used were either "n-fatty alcohols" for the long carbon chains or methanol for the single carbon addition.

For Example 11, esterification was performed as follows: To a 1 liter flask, gamma-butyrolactone (90.0 grams, 1.045 mol, 1.0 equiv.) was added along with isoamyl alcohol (170.8 mL, 1.5675 mol, 1.5 equiv), toluene (560 mL) and $H_2SO_4$ (5 mL). The mixture was brought to reflux for 16 hours. The mixture was cooled and partitioned with water (100 mL). The biphasic mixture was separated, and the aqueous phase washed with hexanes (2×100 mL). The combined organics were washed with sodium bicarbonate (saturated aqueous, 50 mL) followed by brine (50 mL), then dried with MgSO$_4$, filtered, and concentrated in vacuo. The residual oil was distilled at reduced pressure (210 mTorr, 62-89° C.) to provide a colorless oil which was then subjected to the reaction of formula II instead of the lactate ester. Purity was confirmed by $^1$H NMR and GCMS prior to use.

The reaction for Examples 1-9 and 12 with the alkyl halide and the esterified product is shown in Reaction scheme (3):

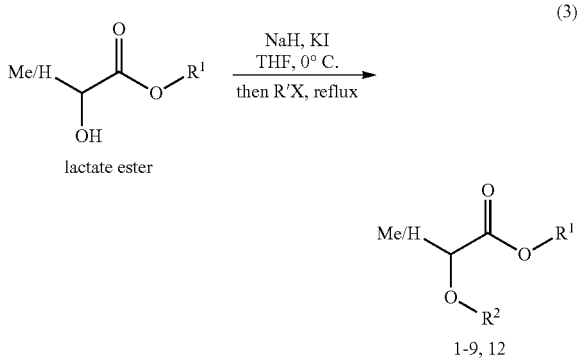

In the reaction of reaction scheme (3), a 500-mL round bottom flask was charged with NaH (60% dispersion in mineral oil) (1.1-1.5 equiv.) and THF (0.5 M), then cooled to 0° C. with an ice bath. To this mixture, the alcohol (1 equiv.) was added via addition funnel over 20 minutes and stirred for 10 minutes. The desired alkyl halide (R'X) (1.1-2.0 equiv.) and KI (0.1 equiv.) were added via graduated cylinder and the reaction mixture was brought to reflux for 16 hours. Once the starting material was consumed as determined by TLC and GCMS, the reaction was cooled to 0° C. and quenched via slow addition of H$_2$O (50 mL), extracted using hexanes (2×50 mL), washed with saturated NaCl solution (50 mL), dried using anhydrous MgSO$_4$, filtered, and concentrated in vacuo. Yields were based on nonoptimized conditions.

Example 11 was converted to an alkoxyalkanoate by a similar method as shown in reaction scheme (3) except the R$^3$ group (per formula I) is different.

Further synthesis information post-esterification and analytical data on Examples 1-12 follow below.

Ethyl 2-ethoxypropanoate (Example 1): Prepared from ethyl lactate (60.4 g, 0.511 mol, 1 equiv) and ethyl bromide. The crude reaction mixture was purified by bulb-to-bulb distillation under reduced pressure (1 atm, 135-150° C.) to afford Example 1 (62.4 g, 84%) as a colorless oil. $^1$H NMR (500 MHz, Chloroform-d) δ 4.16-4.06 (m, 2H), 3.85 (m, 1H), 3.51 (m, 1H), 3.34 (m, 1H), 1.32-1.28 (m, 3H), 1.20-1.16 (m, 3H), 1.15-1.10 (m, 3H).

Isobutyl 2-isobutoxypropanoate (Example 2): Prepared from isobutyl 2-hydroxypropanoate (78.0 g, 0.534 mol, 1 equiv.) and 1-bromo-2-methyl propane. The crude reaction mixture was purified by bulb-to-bulb distillation under reduced pressure (190 mTorr, 55-81° C.) to afford Example 2 (33.0 g, 32%) as a colorless oil. $^1$H NMR (500 MHZ, Chloroform-d) δ 3.96-3.87 (m, 3H), 3.35 (dd, J=8.1, 6.5 Hz, 1H), 3.10 (dd, J=8.9, 6.8 Hz, 1H), 1.95 (septet, J=6.7 Hz, 1H), 1.87 (septet, J=6.6 Hz, 1H), 1.40 (d, J=6.9 Hz, 3H), 0.93 (d, J=6.7 Hz, 3H), 0.91 (d, J=6.7 Hz, 3H).

Isopentyl 2-isopentyloxypropanoate (Example 3): Prepared from isopentyl 2-hydroxypropanoate (50.0 g, 0.312 mol, 1 equiv.) and 1-bromo-3-methylbutane. The crude reaction mixture was purified by bulb-to-bulb distillation under reduced pressure (100 mTorr, 60-65° C.) to afford Example 3 (35.8 g, 49%) as a colorless oil. $^1$H NMR (500 MHz, Chloroform-d) δ 4.14-4.05 (m, 2H), 3.84 (q, J=6.8 Hz, 1H), 3.50 (q, J=6.9 Hz, 1H), 3.30 (q, J=6.8 Hz, 1H), 1.63 (nonet, J=6.6 Hz, 2H), 1.47 (q, J=7.0 Hz, 2H), 1.41 (dq, J=6.8, 2.6 Hz, 2H), 1.30 (d, J=7.1 Hz, 3H), 0.85 (dd, J=6.7, 2.0 Hz, 6H), 0.82 (dd, J=6.7, 1.4 Hz, 6H).

Methyl 2-butoxypropanoate (Example 4): Prepared from methyl lactate (60.0 g, 0.576 mol, 1 equiv.) and 1-bromobutane. The crude reaction mixture was purified by bulb-to-bulb distillation under reduced pressure (140 mTorr, 65-81° C.) to afford Example 4 (54.0 g, 59%) as a colorless oil. $^1$H NMR (500 MHz, Chloroform-d) δ 3.94 (q, J=6.8 Hz, 1H), 3.71 (s, 3H), 3.52 (dt, J=8.9, 6.6 Hz, 1H), 3.33 (dt, J=9.0, 6.7 Hz, 1H), 1.55 (dq, J=8.0, 6.8 Hz, 2H), 1.36 (d, J=6.8 Hz, 3H), 0.88 (t, J=7.4 Hz, 3H).

Methyl 2-hexyloxypropanoate (Example 5): Prepared from methyl lactate (60.0 g, 0.576 mol, 1 equiv.) and 1-bromohexane. The crude reaction mixture was purified by bulb-to-bulb distillation under reduced pressure (240 mTorr, 55-72° C.) to afford Example 5 (41.0 g, 38%) as a colorless oil. $^1$H NMR (500 MHZ, Chloroform-d) δ 3.96 (q, J=6.9 Hz, 1H), 3.72 (s, 3H), 3.52 (dt, J=8.9, 6.7 Hz, 1H), 3.33 (dt, J=8.9, 6.8 Hz, 1H), 1.65-1.48 (pent, J=6.8 Hz, 2H), 1.38 (d, J=6.8 Hz, 3H), 1.27 (d, J=3.6 Hz, 6H), 0.86 (t, J=6.8 Hz, 3H).

Methyl 2-octyloxypropanoate (Example 6): Prepared from methyl lactate (52.0 g, 0.500 mol, 1 equiv.) and 1-bromooctane. The crude reaction mixture was purified by bulb-to-bulb distillation under reduced pressure (20 Torr, 135-150° C.) to afford Example 6 (36.8 g, 34%) as a colorless oil. $^1$H NMR (500 MHz, Chloroform-d) δ 3.91 (q, J=6.5 Hz, 1H), 3.69 (s, 3H), 3.50 (q, J=7.9 Hz, 1H), 3.36-3.24 (m, 1H), 1.58-1.51 (m, 2H), 1.35 (d, J=6.7 Hz, 3H), 1.31-1.17 (m, 10H), 0.85-0.80 (m, 3H).

Octyl 2-methoxypropanoate (Example 7): Prepared from n-octyl lactate (163 g, 0.800 mol, 1 equiv.) and iodomethane. The crude reaction mixture was purified by bulb-to-bulb distillation under reduced pressure (560 mTorr, 65° C.) to afford Example 7 (64.5 g, 37%) as a colorless oil. $^1$H NMR (500 MHz, Chloroform-d) δ 4.04 (q, J=6.3 Hz, 2H), 3.75 (q, J=6.9 Hz, 1H), 3.27 (s, 3H), 1.60-1.45 (m, 2H), 1.28 (d, J=7.0 Hz, 3H), 1.25-1.12 (m, 10H), 0.77 (t, J=6.8 Hz, 3H).

Ethyl 2-octyloxypropanoate (Example 8): Prepared from ethyl lactate (60.0 g, 0.508 mol, 1 equiv.) and 1-bromooctane. The crude reaction mixture was purified by bulb-to-bulb distillation under reduced pressure (650 mTorr, 69-76° C.) to afford Example 8 (50.0 g, 48%) as a colorless oil. $^1$H NMR (500 MHz, Chloroform-d) δ 4.17 (p, J=7.0 Hz, 2H), 3.90 (q, J=6.8 Hz, 1H), 3.52 (dt, J=8.8, 6.7 Hz, 1H), 3.32 (dt, J=8.9, 6.7 Hz, 1H), 1.67-1.46 (m, 2H), 1.36 (d, J=6.8 Hz, 3H), 1.26 (t, J=7.2 Hz, 13H), 0.84 (t, J=6.8 Hz, 3H).

Methyl 2-methylcyclopropyloxypropanoate (Example 9): Prepared from methyl lactate (60.0 g, 0.576 mol, 1 equiv.) and (bromomethyl)cyclopropane. The crude reaction mixture was purified by bulb-to-bulb distillation under reduced pressure (2.80 Torr, 62-71° C.) to afford Example 9 (39.0 g, 43%) as a colorless oil. $^1$H NMR (500 MHZ, Chloroform-d) δ 4.00 (ddd, J=6.9, 4.7, 2.3 Hz, 1H), 3.77-3.64 (m, 3H), 3.33-3.25 (m, 2H), 1.41-1.37 (m, 3H), 1.16-0.94 (m, 1H), 0.61-0.43 (m, 2H), 0.22-0.16 (m, 2H).

"B100" 2-methoxypropanoate (Example 10): Prepared from "B100" lactate (50.0 g, 0.147 mol, 1 equiv.) and iodomethane. The crude reaction mixture was purified by bulb-to-bulb distillation under reduced pressure (860 mTorr, 161-184° C.) to afford Example 10 (56.3 g, 47% over two steps) as a colorless oil. $^1$H NMR (500 MHZ, Chloroform-d) δ 5.47-5.21 (m, 2.4H), 4.14 (td, J=6.7, 5.0 Hz, 2H), 3.86 (q, J=6.8 Hz, 1H), 3.38 (s, 3H), 2.76 (t, J=6.3 Hz, 0.5H), 2.12-1.84 (m, 4H), 1.76-1.57 (m, 3H), 1.39 (d, J=6.9 Hz, 4H), 1.34-1.24 (m, 23H), 0.95-0.70 (m, 3H).

isopentyl 4-(isopentyloxy)butanoate ((Example 11): Prepared from isopentyl 4-hydroxybutanoate (0.546 mol, 1 equiv) and 1-bromo-3-methylbutane. The crude reaction mixture was purified by bulb-to-bulb distillation under reduced pressure (1.19 Torr, 95-114° C.) to afford Example 11 as a colorless oil. $^1$H NMR (500 MHZ, Chloroform-d) δ 4.10 (t, J=6.9 Hz, 2H), 3.42 (td, J=6.5, 4.2 Hz, 4H), 2.38 (t, J=7.4 Hz, 2H), 1.88 (ddd, J=13.8, 7.5, 6.3 Hz, 2H), 1.78-1.58 (m, 2H), 1.51 (q, J=6.9 Hz, 2H), 1.44 (q, J=6.9 Hz, 2H), 0.90 (dd, J=12.0, 6.7 Hz, 12H).

isopentyl 2-(isopentyloxy)acetate (Example 12): Prepared from isopentyl 2-hydroxyacetate (64.9 g, 0.443 mol, 1 equiv.) and 1-bromo-3-methylbutane. The crude reaction mixture was purified by bulb-to-bulb distillation under reduced pressure (1 atm, 105-108° C.) to afford Example 12 (32.0 g, 34%) as a colorless oil. $^1$H NMR (500 MHz, Chloroform-d) δ 4.18 (t, J=6.9 Hz, 2H), 4.04 (s, 2H), 3.54 (t, J=6.8 Hz, 2H), 1.69 (nonet, J=6.9 Hz, 2H), 1.52 (dq, J=13.6, 6.9 Hz, 4H), 0.91 (t, J=5.3 Hz, 14H).

Example 13 Property Tests

Examples 1-12 are shown in Table 2 with test properties for DCN (diesel cetane number), LHV (lower heating value), and CP (cloud point). YSI (yield sooting index) values were provided based on experimental measurement by an outside laboratory. Calculations based on Montgomery et al "Analyzing the robustness of the yield sooting index as a measure of sooting tendency" Proc. Combust. Inst. 2018 (incorporated herein by reference).

Fuel properties of the various molecules investigated in this study were tested following ASTM protocols in partnership with Intertek Inc. in Benecia, CA, which is a commercial testing facility. Derived Cetane Number (DCN) was determined by Ignition Quality Test (IQT) according to ASTM D6890 protocol (ASTM-D6890-16e1, 2016) [9B], and No-Flow Point according to ASTM D7346 protocol (ASTM-D7346-15, 2015) [9C]. Higher Heating Value (HHV) was determined by ASTM D240 protocol (ASTM-D240-19, 2019) [9D] and the Lower Heating Value (LHV) was calculated based on the higher heating value using the equation developed by Lloyd (referenced in ASTM D240 method) which is shown below as equation 1. [10A]

LHV [MJ/kg]=HHV [MJ/kg]−(0.2122*mass % hydrogen)  Eqn. 1

TABLE 3

| Compound | Structure | C:O ratio | DCN | LHV (MJ/kg) | YSI | CP (° C.) |
|---|---|---|---|---|---|---|
| EXAMPLE-1 | 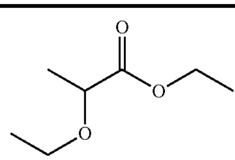 | 2.33333 | 23.1 | 25.48 | 22 +/− 8.9 | <−50 |
| EXAMPLE-2 | 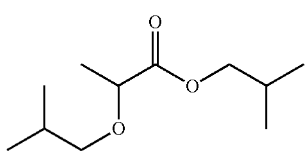 | 3.66667 | 47.6 | 25.3 | 58.5 +/− 9.3 | −50 |
| EXAMPLE-3 | 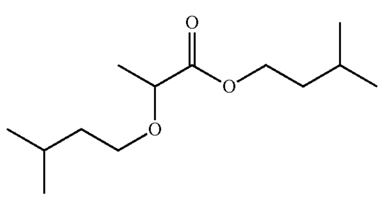 [SMILES: CC(C)CCOC(=O)C(C)OCCC(C)C] | 4.33333 | 43.6 | 34.5 | 71.3 +/− 9.4 | <−50 |
| EXAMPLE-4 | 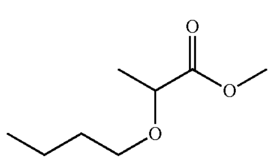 | 2.66667 | 46.3 | 27.1 | 30 +/− 8.9 | <−60 |
| EXAMPLE-5 | 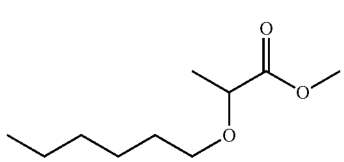 | 3.33333 | 53.4 | 29.5 | 42.8 +/− 8.9 | <−60 |

TABLE 3-continued

| Compound | Structure | C:O ratio | DCN | LHV (MJ/kg) | YSI | CP (° C.) |
|---|---|---|---|---|---|---|
| EXAMPLE-6 | 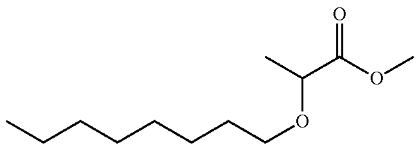 | 4 | 59.4 | 30.79 | 55.6 +/− 9.0 | <−50 |
| EXAMPLE-7 | 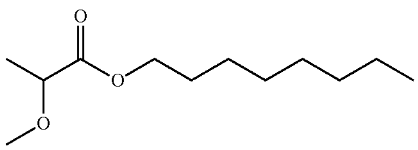 | 4 | 57.5 | 31.71 | 55.6 +/− 9.0 | <− 50 |
| EXAMPLE-8 | 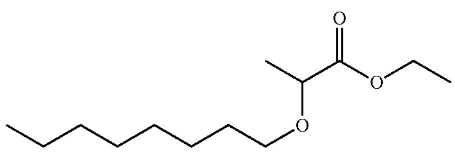 [SMILES: CCCCCCCCOC(C)C(=O)OCC] | 4.33333 | 62.2 | 32.2 | 60.5 +/− 9.1 | <− 60 |
| EXAMPLE-9 | 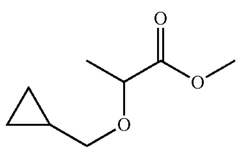 | 3 | 10 | 27 | 53.8 +/− 67.4 | −60 |
| EXAMPLE-10 | 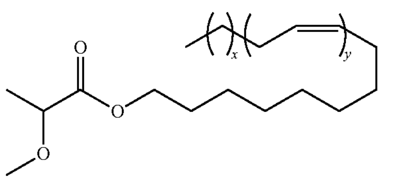 | 7.33333 | 82.7 | 36.5 | 144.2 +/− 12.3 | −10 |
| EXAMPLE-11 | 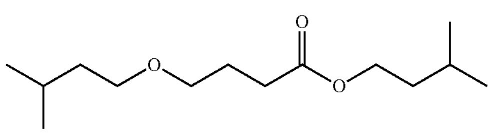 [SMILES: CC(C)CCOCCCC(=O)OCCC(C)C] | 4.66667 | 61.7 | 32.5 | 81.9 +/− 9.4 | <− 60 |
| EXAMPLE-12 | | 4 | 47.1 | 31.8 | 69.1 +/− 9.3 | <− 60 | x is 1-8, and y is 0 to 3

Figure 2:
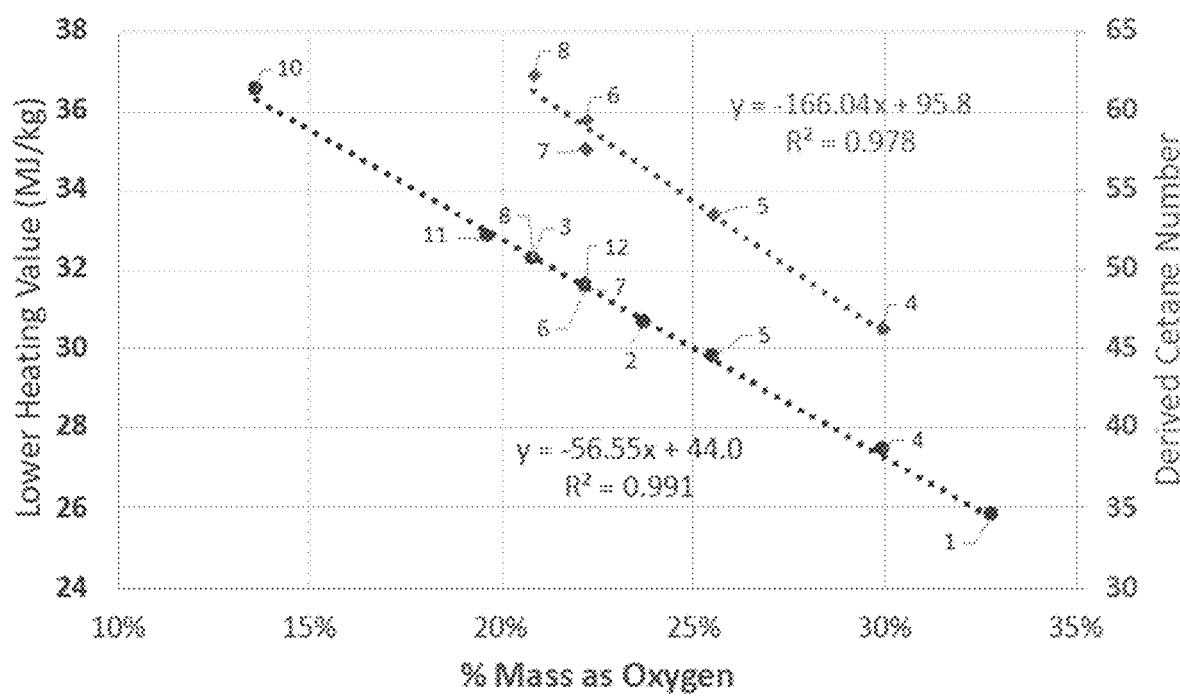
FIG. 2 is a graph showing the DCN, LHV, and percent by mass of oxygen of several example compounds.

A graphical representation of some of this data is shown in FIG. 2, which compares the DCN, LHV, and percent by mass of oxygen. The darker plot to the lower left is the LHV data, and the lighter plot to the upper right is the DCN data.

Figure 3:
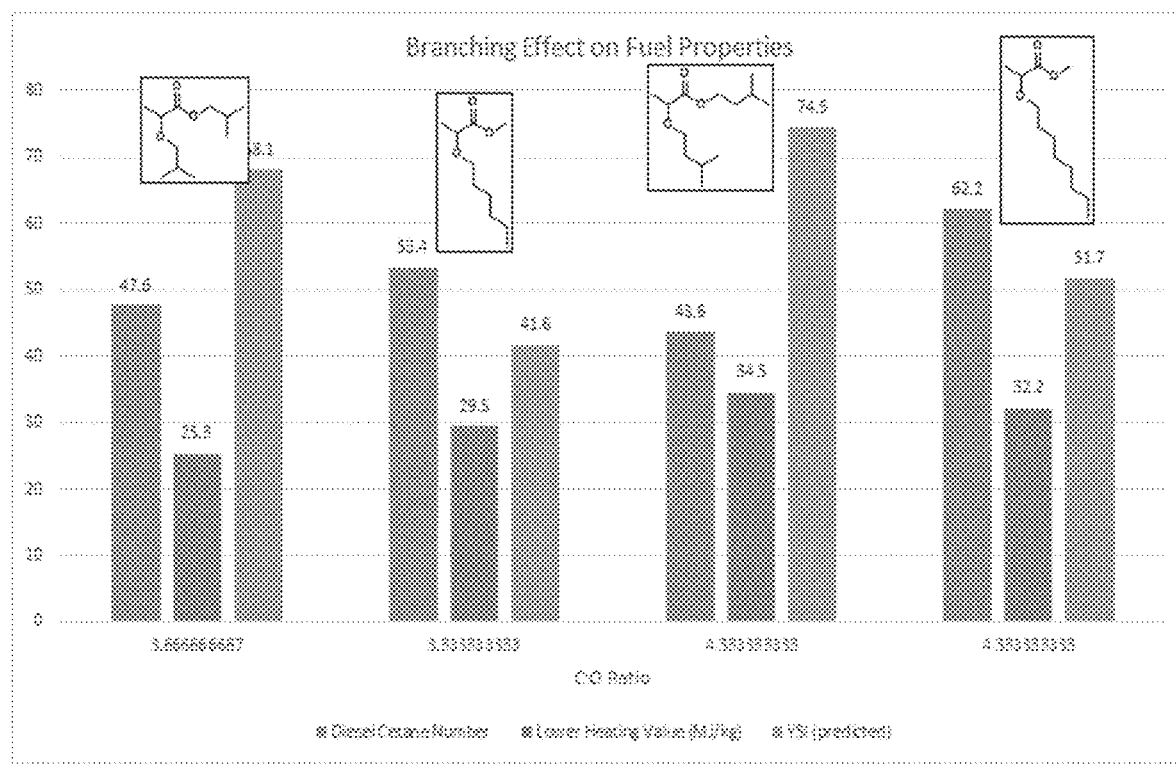
FIG. 3 is a graph showing the effect of branching on properties of example alkoxyalkanoate compounds.

FIG. 3 shows another graphical representation of DCN, LHV, and YSI properties for Examples 2, 5, 3, and 6, in order from left to right. These were the best performing Examples.

Figure 4:
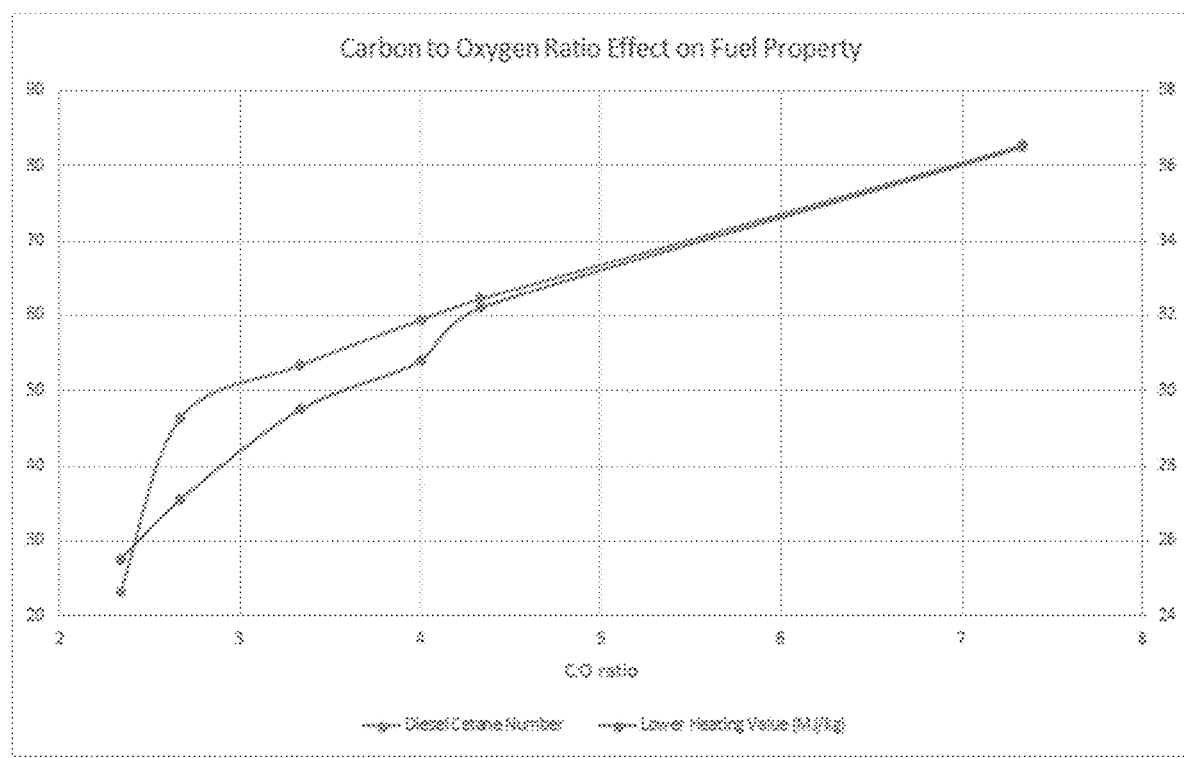
FIG. 4 is a graph showing the effect of carbon to oxygen ratio on fuel properties.

FIG. 4 shows a plot of Examples 1, 4, 5, 6, 8, and 10 (in order from left to right) based on their carbon to oxygen ratios (x-axis) versus their DCN (left y-axis) and LHV (right y-axis) properties. The plot that is lower for the majority of the graph is the LHV data, the higher plot is the DCN data.

The data presented in FIGS. 2, 3, and 4 offer insights into structure/property relationships for the alkoxyalkanoate molecules. Comparing these Examples 2 and 3 versus 5, it is evident that if two molecules have a similar number of carbons, the asymmetric one with one short carbon chain and one longer carbon chain will have a higher DCN.

As seen in Table 1 and FIG. 2, when comparing several Examples, it can be seen that for unsymmetrical structures with one short chain and one long chain, increasing the length of the long chain results in an increase in DCN and LHV, but also increasing the amount of soot formed. Interestingly, when an additional carbon is added to the short chain, the DCN and LHV continue to increase, but the amount of soot formed per unit mass decreases. While the mechanism for this reduced soot formation is unknown, the result suggests that once one carbon chain is sufficiently long to increase the DCN into the acceptable range, increasing the length of the short carbon chain is the most optimal way to continue to increase LHV while minimizing soot formation.

Comparing Examples 3, 8, 12 shows that adding branching to the carbon chain decreases the DCN, has a negligible impact on LHV (Examples 3 and 8 have the same molecular formula and almost identical LHVs), and significantly increases the amount of soot formed.

Based on these results, Example 8 (ethyl lactate octyl ether) appears to be the most preferred structure when considering all properties investigated in this series, with Example 4 (methyl lactate butyl ether) would be preferred if soot reduction was the primary consideration.

Example 14: Location of Long Alkyl Chain

The test data was also explored to determine if the arrangement of the short chain and long chain on the alkoxyalkanoate had an impact on DCN or LHV. Since YSI has been shown to be accurately predictable based on a group contribution method and the groups between Examples 6 and 7 are identical, sooting tendency was not considered in this series. See St John et al "A quantitative model for the prediction of sooting tendency from molecular structure" Energy and Fuels (2017) 31, 9, 9983-9990, incorporated herein by reference.

Figure 5:
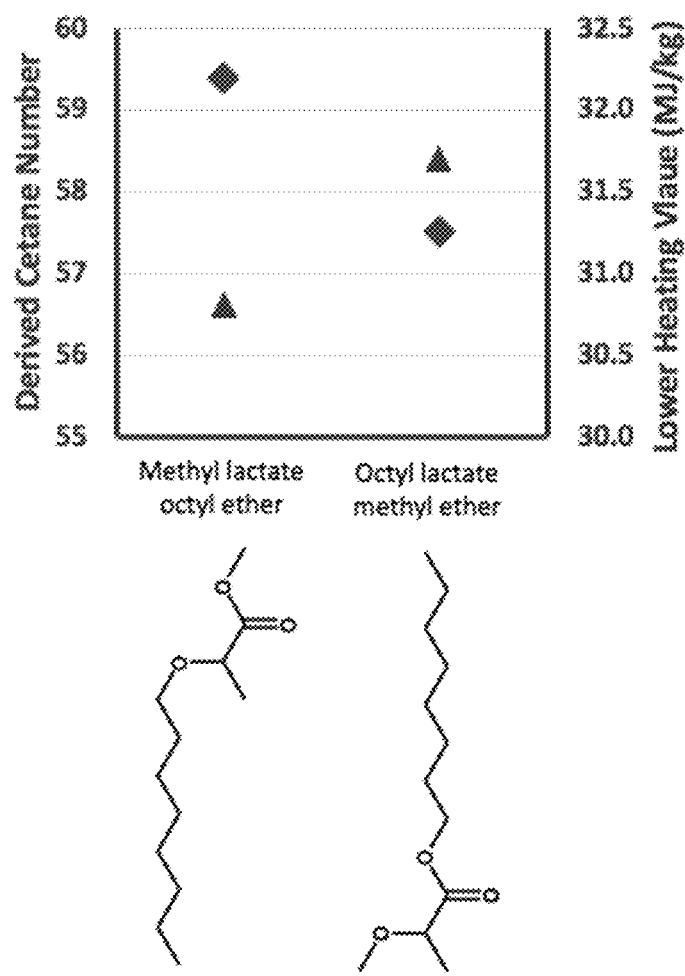
FIG. 5 is a graph showing fuel property effects of whether a long chain alkyl group is associated with an ether moiety or ester moiety.

FIG. 5 compares the DCN and LHV of Examples 6 and 7, which are two $C_{12}H_{24}O_3$ isomers with two possible arrangements of the short chain and long chain. Methyl lactate octyl ether corresponds to the diamonds on the graph, while the octyl lactate methyl ether corresponds to the triangles on the graph. This figure and data illustrates that having the longer chain bound as an ether ($R^1$ group per formula I), with the shorter chain bound as an ester ($R^2$ group per formula I) leads to a higher DCN than vice-versa, while LHV is not significantly affected. While the difference between the DCN values is <2, it is large enough to be beyond the expected repeatability error of the measurement.

Example 15: Backbone Length

Figure 6:
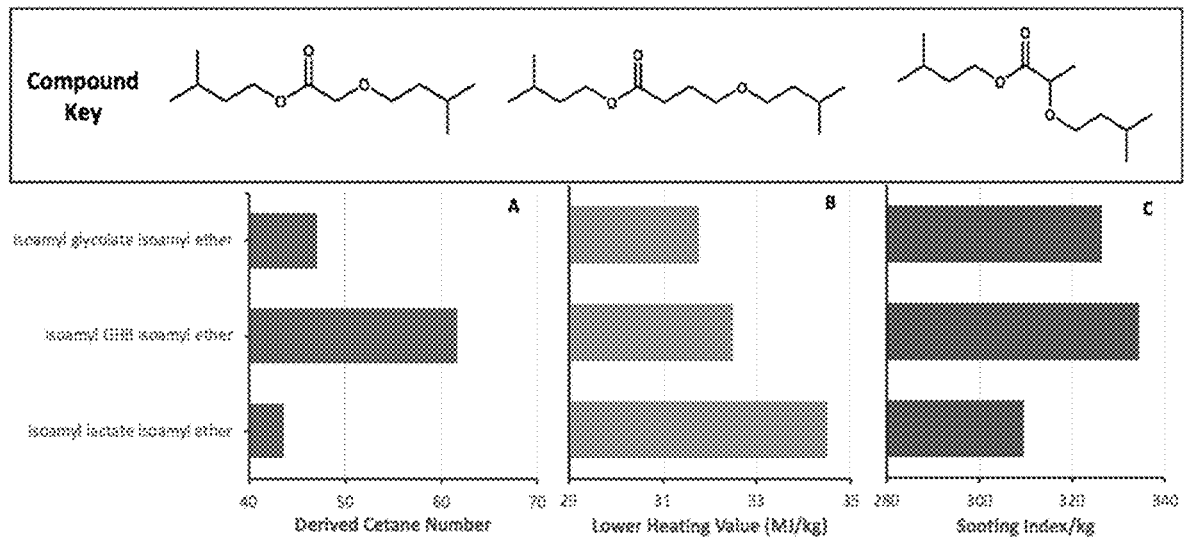
FIG. 6 is a graph showing the effect of a different alkoxyalkanoate backbone group on the fuel properties of the composition.

FIG. 6 illustrates an investigation of different hydroxyalkanoate backbone structures ($R^3$ group per Formula I) on fuel properties for alkoxyalkanoates. The impact that the hydroxyalkanoate "backbone" has on each of the three fuel properties was investigated and is highlighted in FIG. 3. While it was shown previously that branching on the exterior carbon chains decreased DCN, increased soot formation, and didn't affect LHV, it appears that the branching on the interior "backbone" of Example 3 still decreases DCN but increases LHV and decreases the amount of soot formed. Accordingly, while each hydroxyalkanoate investigated led to molecules with acceptable fuel properties in all three categories, the use of lactate as a backbone had the highest LHV and least amount of soot formed.

All patents, patent applications, publications, technical and/or scholarly articles, and other references cited or referred to herein are in their entirety incorporated herein by reference to the extent allowed by law. The discussion of those references is intended merely to summarize the assertions made therein. No admission is made that any such patents, patent applications, publications or references, or any portion thereof, are relevant, material, or prior art. The right to challenge the accuracy and pertinence of any assertion of such patents, patent applications, publications, and other references as relevant, material, or prior art is specifically reserved.

In the description above, for the purposes of explanation, numerous specific details have been set forth in order to provide a thorough understanding of the embodiments. It will be apparent however, to one skilled in the art, that one or more other embodiments may be practiced without some of these specific details. The particular embodiments described are not provided to limit the invention but to illustrate it. The scope of the invention is not to be determined by the specific examples provided above but only by the claims below.

What has been described above includes examples of one or more embodiments. It is, of course, not possible to describe every conceivable modification and alteration of the above devices or methodologies for purposes of describing the aforementioned aspects, but one of ordinary skill in the art can recognize that many further modifications and permutations of various aspects are possible. Accordingly, the described aspects are intended to embrace all such alterations, modifications, and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim. The term "consisting essentially" as used herein means the specified materials or steps and those that do not materially affect the basic and novel characteristics of the material or method. Unless the context indicates otherwise, all percentages and averages are by weight. If not specified above, the properties mentioned herein may be determined by applicable ASTM standards, or if an ASTM standard does not exist for the property, the most commonly used standard known by those of skill in the art may be used. The articles "a," "an," and "the," should be interpreted to mean "one or more" unless the context indicates the contrary.

What is claimed is:

1. A fuel for an internal combustion engine comprising: a $C_7$ to $C_{22}$ alkoxyalkanoate corresponding to formula (I):

(I)

wherein $R^2$ and $R^1$ are alkyl groups independently selected to have 2 to 18 carbon atoms; and
wherein the $R^3$ group is a $C_1$ to $C_5$ group divalent alkyl group; and
$R^1$ and $R^2$ have a different number of carbon atoms; or
$R^1$ and $R^2$ are independently selected to have 8 to 18 carbon atoms; or
$R^1$ and $R^2$ have 1 to 3 branching methyl or ethyl or propyl groups;
wherein either or both $R^1$ and $R^2$ have a cyclic group with 3 to 6 members or 1 to 5 units of unsaturation.

2. The fuel of claim 1, wherein $R^1$ and $R^2$ have a different number of carbon atoms.

3. The fuel of claim 1, wherein $R^1$ and $R^2$ have 1 to 3 branching methyl or ethyl or propyl groups.

4. The fuel of claim 1, wherein both $R^1$ and $R^2$ have a cyclic group with 3 to 6 members or 1 to 5 units of unsaturation.

5. The fuel of claim 1, wherein one of $R^1$ and $R^2$ is a $C_1$ or $C_2$ alkyl group, and the other is a $C_4$ to $C_8$ group.

6. The fuel of claim 5, wherein $R^3$ is —CH(CH$_3$)—.

7. The fuel of claim 1, wherein $R^3$ is —CH(CH$_3$)—.

8. The fuel of claim 1, wherein the alkoxyalkanoate is derived from a renewable biomass source.

9. The fuel of claim 1, wherein the alkoxyalkanoate has an LHV of 25 to 40 MJ/kg.

10. The fuel of claim 1, wherein the alkoxyalkanoate has a cloud point of −5° C. to −100° C.

11. A blended fuel for an internal combustion engine comprising:
   a fuel selected from the group consisting of: gasoline, diesel, alcohol fuel, biofuel, Fischer-Tropsch fuel, or combinations thereof; and
   a $C_7$ to $C_{22}$ alkoxyalkanoate corresponding to formula (I):

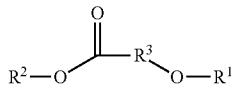

(I)

wherein $R^2$ and $R^1$ are alkyl groups independently selected to have 2 to 18 carbon atoms; and
   wherein the $R^3$ group is a $C_1$ to $C_5$ group divalent alkyl group; and
   $R^1$ and $R^2$ have a different number of carbon atoms; or
   $R^1$ and $R^2$ are independently selected to have 8 to 18 carbon atoms; or
   $R^1$ and $R^2$ have 1 to 3 branching methyl or ethyl or propyl groups;
   wherein an effective of amount of the alkoxyalkanoate is present to lower a cloud point of the blended fuel 5 to 50° C. lower than the fuel alone.

12. The blended fuel of claim 11, wherein the alkoxyalkanoate is present in a ratio of 99.9:0.1 to 51:49 by volume to the fuel.

13. The blended fuel of claim 12, wherein the fuel is selected from the group consisting of diesel, biofuel, alcohol, or a combination of these.

14. The blended fuel of claim 11, wherein the fuel is present in a ratio of 99.9:0.1 to 51:49 by volume to the alkoxyalkanoate.

15. The blended fuel of claim 14, wherein the fuel is selected from the group consisting of diesel, biofuel, alcohol, or a combination of these.

16. The blended fuel of claim 11, wherein the fuel is selected from the group consisting of diesel, biofuel, alcohol, or a combination of these.

17. A method for making a fuel product for an internal combustion engine at least partially from a biomass source, the method comprising:
   reacting a fusel alcohol and hydroxyalkanoate in a solvent to form a hydroxyalkanoate; and
   reacting the hydroxyalkanoate with an alkyl halide to form an alkoxyalkanoate;
   wherein the alkoxyalkanoate is an asymmetric $C_7$ to $C_{22}$ alkoxyalkanoate; or a $C_{12}$ to $C_{22}$ alkoxyalkanoate; or the alkoxyalkanoate includes 1 to 3 branching methyl or ethyl or propyl groups on an ether-bound end and 1 to 3 branching methyl or ethyl or propyl groups on an ester-bound end;
   further comprising the step of blending the alkoxyalkanoate with a fuel selected from the group consisting of: gasoline, diesel, alcohol fuel, biofuel, Fischer-Tropsch fuel, or combinations thereof;
   wherein an effective amount of alkoxyalkanoate is blended in the blending step to lower a cloud point of the fuel product 5 to 50° C. lower than the fuel alone.

18. The method of claim 17, further comprising adding an acid catalyst in the step of reacting a fusel alcohol and hydroxyalkanoate in a solvent to form a hydroxyalkanoate.

19. The method of claim 17, wherein the alkoxyalkanoate corresponds to formula (I):

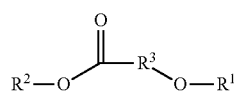

(I)

wherein $R^2$ and $R^1$ are alkyl groups independently selected to have 2 to 18 carbon atoms; and
   wherein the $R^3$ group is a $C_1$ to $C_5$ group divalent alkyl group.

20. The method of claim 17 further comprising producing the hydroxyalkanoate and fusel alcohol from the biomass source through acidogenic or solvetogenic biochemical pathways in homo- or heterofermentative processes.

* * * * *